US00PP33156P2

(12) United States Plant Patent
Bradford et al.

(10) Patent No.: US PP33,156 P2
(45) Date of Patent: Jun. 15, 2021

(54) PEACH TREE NAMED 'PEARL PRINCESS VI'

(50) Latin Name: *Prunus persica*
Varietal Denomination: Pearl Princess VI

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 16/974,332

(22) Filed: Jan. 4, 2021

(51) Int. Cl.
*A01H 5/08* (2018.01)
*A01H 6/74* (2018.01)

(52) U.S. Cl.
USPC ..... Plt./195
CPC ..... *A01H 6/7463* (2018.05)

(58) Field of Classification Search
USPC ..... Plt./195
CPC ..... A01H 5/0868
See application file for complete search history.

(56) References Cited

U.S. PATENT DOCUMENTS

PP19,919 P2 4/2009 Bradford

*Primary Examiner* — Kent L Bell

(57) ABSTRACT

The present invention relates to a new and distinct variety of peach tree, *Prunus persica*, broadly characterized by a medium size, vigorous, hardy, self-fertile, productive and regular bearing tree. The variety blooms during mid season and requires about 550 chilling hours. The fruit matures under the ecological conditions described in mid to late June, with first picking on Jun. 22, 2020. The fruit is uniform, very large in size, oblate in shape, clingstone in type, firm in texture, almost entirely red in skin color, white in flesh color, and sub-acidic in flavor.

1 Drawing Sheet

Botanical classification: *Prunus persica.*
Variety denomination: 'PEARL PRINCESS VI'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of peach tree, which has been denominated varietally as 'Pearl Princess VI'.

The present variety was hybridized by us in 2008 as a first generation cross using 'Pearl Princess V' (U.S. Plant Pat. No. 19,919) peach as the selected seed parent and '66M351' (unpatented) nectarine as the selected pollen parent. Upon reaching maturity the fruit of this cross was gathered, and the seeds were removed, cracked, stratified, germinated, and grown as seedlings on their own root in our greenhouse. Upon reaching dormancy the seedlings were transplanted as a group to a cultivated area of our experimental orchard located near Le Grand, Calif., in Merced County (San Joaquin Valley). During the fruit evaluation season of 2012, we selected the present variety as a single tree from the group of seedlings described above. Subsequent to origination of the present variety of peach tree, we asexually reproduced it by budding and grafting in the experimental orchard described above, and such reproductions were true to the original tree in all respects. The reproduction of the variety included the use of 'Nemaguard' (unpatented) rootstock upon which the present variety was compatible and true to type.

The present variety is similar to its pollen parent, '66M351' (unpatented) nectarine, by being self-fertile, and by producing fruit that is mostly red in skin color and firm in texture, but is quite distinguished therefrom by being a peach instead of nectarine, by being clingstone instead of freestone, and by ripening about twenty days earlier.

The present variety most similar to its seed parent, 'Pearl Princess V' peach tree (U.S. Plant Pat. No. 19,919), by having a medium size tree, by blooming in the mid season, by having large showy blossoms, by being self-fertile, and by producing white flesh peaches that are mostly red in skin color, firm in texture, and sub-acid in flavor, but is distinguished therefrom by producing peaches that are larger in size, that are mostly oblate instead of globose in shape, that are clingstone instead of freestone in type, and that mature about three days earlier.

SUMMARY OF VARIETY

In summary, the present peach variety is characterized by a medium size, vigorous, hardy, self-fertile, productive and regular bearing tree. The variety blooms during mid season and requires about 550 chilling hours. The fruit matures under the ecological conditions described in mid to late June, with first picking on Jun. 22, 2020. The fruit is uniform, very large in size, oblate in shape, clingstone in type, firm in texture, almost entirely red in skin color, white in flesh color, and sub-acidic in flavor.

DRAWING

The accompanying photograph consists of four whole fruits positioned to display the characteristics of the skin color and form, one divided fruit to reveal the flesh and stone, a tip shoot of new leaf growth, typical leaves, and two insets depicting the flower buds and blossoms as they appeared on the tree during the blooming season.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of shipping ripe on Jul. 2, 2020, on the original tree during its twelfth growing season. The blossom and flower descriptions were made the previous blooming season. All major color code designations are by reference to the Inter-Society Color Council, National Bureau of Standards. Common color names are also used occasionally.

PARENTAGE

Seed parent: 'Pearl Princess V' (U.S. Plant Pat. No. 19,919) peach.

Pollen parent: '66M351' (unpatented) nectarine.

TREE

Size: Medium, reaching and maintaining a height of 8' [2.44 m.] and a spread of 6' [1.83 m.] after twelve growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 550 hours.

Leaf bud burst: Medium to late, during the end of flowering.

Trunk:

- *Size.*—Medium, reaching a maximum diameter of 3" [76 mm.] after the twelfth growing season.
- *Texture.*—Shaggy, medium roughness.
- *Bark color.*—A Grayish yellowish brown [80. gy.yBr] and Moderate yellowish brown [77. m.yBr] variegation with Dark yellowish brown [78. d.yBr] crevices present.
- *Lenticels.*—Approximate Number Per Square Inch: 8. Color: Brownish orange [54. brO]. Average Size: ⅛" [3.2 mm.] in length. The width is typically one fourth as much as the length. Shape: Elongated.

Branches:

- *Size.*—Medium, diameter of main scaffold is 1½" [38.1 mm.] measured 12" above the crotch, diameter of the limb is 1" [25.4 mm.] measured 12" above the first fork.
- *Texture.*—Medium to shaggy.
- *Color.*—1st Year Wood Topside: Grayish red [19. gy.R]. 1st Year Wood Underside: Brilliant yellow green [116. brill.YG]. 2nd Year and Older Wood: A Light grayish brown [60. l.gy.Br] and Brownish gray [64. brGy] variegation with Dark grayish brown [62. d.gy.Br] crevices present.
- *Lenticels.*—Number Per Square Inch: About 50 on second year wood. Color: Strong brown [55. s.Br]. Average Size: Small, 1/16" [1.6 mm.] in length. The width is typically one fourth as much as the length. Shape: Elongated.

Leaves:

- *Size.*—Medium to large. Average Length: 5⅝" [143 mm.]. Average Width: 1 9/16" [39.7 mm.].
- *Arrangement.*—Alternate.
- *Thickness.*—Medium.
- *Form.*—Elliptical.
- *Apex.*—Acuminate.
- *Base.*—Mostly acute with an average base angle of 60 degrees.
- *Surface.*—Smooth on both sides.
- *Color.*—Dorsal Surface: Moderate olive green [125. m.OlG]. Ventral Surface: Moderate yellow green [120. m.YG].
- *Red midvein.*—Absent.
- *Margin.*—Finely serrate.
- *Venation.*—Pinnately net veined.
- *Vein color.*—Light yellow green [119. l.YG].
- *Petiole.*—Average Length: 7/16" [11.1 mm.]. Average Thickness: 1/16" [1.6 mm.]. Color: Moderate yellow green [120. m.YG].
- *Stipules.*—Number: Typically two per leaf, up to six per growing tip. Average Length: ¼" [6.4 mm.]. Color: Vivid yellow green [115. v.YG] becoming Moderate brown [58. m.Br] with maturity.
- *Glands.*—Number: 2 to 4 per leaf. Position: Somewhat alternate, positioned on the petiole near the base of blade. Form: Reniform. Size: Medium, about 1/16" [1.6 mm.] in length.
- *Leaf buds.*—Pointed.

Flower buds:

- *Hardiness.*—Hardy, with respect to central California blooming season.
- *Diameter.*—Typically ⅜" [9.5 mm.] 1 week before bloom.
- *Length.*—Typically ⅝" [15.9 mm.] 1 week before bloom.
- *Form.*—Not appressed.
- *Surface.*—Pubescent.
- *Tip color.*—Light pink [4. l.Pk].

Flowers: Perfect, complete, perigynous, usually a single pistil, about thirty stamens, five sepal and petal locations alternately positioned.

- *Type.*—Showy, large.
- *Average flower diameter.*—1⅞" [47.6 mm.].
- *Average flower depth.*—½" [12.7 mm.] when fully open.
- *Number of petals.*—Mostly five, extra petal fragments are common with a few double blossoms observed.
- *Petal shape.*—Circular to oval.
- *Petal margin.*—Entire, wavy, occasional notches.
- *Average petal diameter.*—¾" [19.1 mm.].
- *Average petal length.*—¾" [19.1 mm.].
- *Petal apex.*—Rounded.

*Petal base.*—Rounded.
*Petal color.*—Light pink [4. l.Pk] toward the apex and Deep pink [3. deep Pk] toward the base on both sides.
*Anthocyanin coloration intensity.*—Weak.
*Anther color.*—Moderate reddish orange [37. m.rO] surrounding a Brilliant yellow [83. brill.Y] center at bloom onset.
*Pollen.*—Anthers produce an abundance of Brilliant yellow [83. brill.Y] pollen.
*Stigma color.*—Light greenish yellow [101. l.gY].
*Stigma position.*—Typically located slightly above the nearby anthers.
*Ovary.*—Pubescent.
*Sepal color.*—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.
*Sepal length.*—¼" [6.4 mm.].
*Sepal width.*—¼" [6.4 mm.].
*Sepal apex.*—Rounded to elliptical to match the sepal length and width.
*Sepal margin.*—Fairly smooth.
*Sepal outer surface.*—Pubescent.
*Average pistil length.*—11/16" [17.5 mm.].
*Average stamen length.*—½" [12.7 mm.].
*Fragrance.*—Moderate.
*Blooming period.*—Medium, blooms about two days after 'Snow Princess' (U.S. Plant Pat. No. 12,570) peach.
*Onset of bloom.*—One percent on Feb. 19, 2020.
*Date of full bloom.*—Feb. 28, 2020.
*Duration of bloom.*—One to two weeks, dependent on ambient temperature.
*Bloom density.*—Heavy.
*Number per cluster.*—1 to 3 with single flowers most common.

FRUIT

Maturity when described: Firm ripe, Jul. 2, 2020.
Date of first picking: Jun. 22, 2020.
Date of last picking: Jul. 4, 2020.
Size: Uniform, large.
*Average diameter axially.*—3⅛" [79.4 mm.].
*Average diameter across suture plane.*—3⅝" [92.1 mm.].
*Average diameter across cheek plane.*—3⅝" [92.1 mm.].
*Typical weight.*—10.6 ounces [300 grams].
Form: Uniform, oblate, symmetrical.
*Longitudinal section form.*—Oblate.
*Axial view.*—Round.
Suture: A very inconspicuous line located in a shallow trough extending from the base to just beyond the pistil point.
*Near the base.*—A very shallow trough.
*Along the side.*—A very shallow trough.
*Near the apex.*—A shallow groove.
Ventral surface: Rounded.
Lips: Lipped on both sides. Lips are fairly equal.
Cavity: Flaring, Light orange yellow [70. l.OY] stem markings typical.
*Depth.*—7/16" [11.1 mm.].
*Breadth.*—1¼" [31.8 mm.].
Base: Truncate, slightly cordate if viewed parallel to the suture.
Apex: Rounded.
Pistil point: An apical Dark brown [59. d.Br] dot, negligible length.
Stem: Medium.
*Average length.*—⅜" [9.5 mm.].
*Average width.*—3/16" [4.8 mm.].
Skin:
*Thickness.*—Medium.
*Surface.*—Pubescent.
*Density of the pubescence.*—Medium to light.
*Down.*—Very short, does not roll up when rubbed.
*Tenacity.*—Tenacious to flesh.
*Astringency.*—Non-astringent.
*Tendency to crack.*—None observed.
*Color.*—Very deep red [14. v.deep R] over a Strong pink [2. s.Pk] background with a few Pale yellowish pink [31. p.yPk] areas where sun protected.
Flesh:
*Color.*—Yellowish white [92. yWhite] with very slight Light pink [4. l.Pk] flecking toward the skin and stone.
*Surface of pit cavity.*—Covered with Yellowish white [92. yWhite] and Pinkish white [9. pkWhite] fibers when twisted from the stone.
*Amygdalin.*—Wanting.
*Juice.*—Scant.
*Texture.*—Very firm.
*Fibers.*—Few and fine.
*Ripens.*—Fairly even, slightly earlier at the shoulders.
*Flavor.*—Sweet and subacid, typically 16 brix.
*Aroma.*—Wanting.
*Eating quality.*—Very good.

STONE

Type: Clingstone.
Form: Oval.
Hilum: Narrow.
Base: Truncated.
Apex: Rounded to acute.
Sides: Fairly equal.
Tip: Negligible.
Surface: Irregularly furrowed near the apex, pitted toward the base.
Ridges: Rounded.
External color: Light yellowish brown [76. l.yBr].
Pit wall color when cracked: Moderate olive brown [95. m.OlBr].
Cavity surface color: Light yellowish brown [76. l.yBr].
Average pit wall thickness: ¼" [6.4 mm.].
Average length: 1 9/16" [39.7 mm.].
Average width: 1⅛" [28.6 mm.].
Average breadth: ⅞" [22.2 mm.].
Tendency to split: None observed.
Kernel:
*Form.*—Oval.
*Skin color.*—Pale yellow [89. p.Y] when first removed.
*Pellicle color.*—Deep brown [56. deep Br].
*Vein color.*—Light yellow [86. l.Y].
*Taste.*—Bitter.
*Viable.*—Yes.
*Average length.*—13/16" [20.6 mm.].

*Average width.*—½" [12.7 mm.].
*Amygdalin.*—Scant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach tree, substantially as illustrated and described, that is most similar to its seed parent, 'Pearl Princess V' peach tree (U.S. Plant Pat. No. 19,919), by having a medium size tree, by blooming in the mid season, by having large showy blossoms, by being self-fertile, and by producing white flesh peaches that are mostly red in skin color, firm in texture, and sub-acid in flavor, but is distinguished therefrom by producing peaches that are larger in size, that are mostly oblate instead of globose in shape, that are clingstone instead of freestone in type, and that mature about three days earlier.

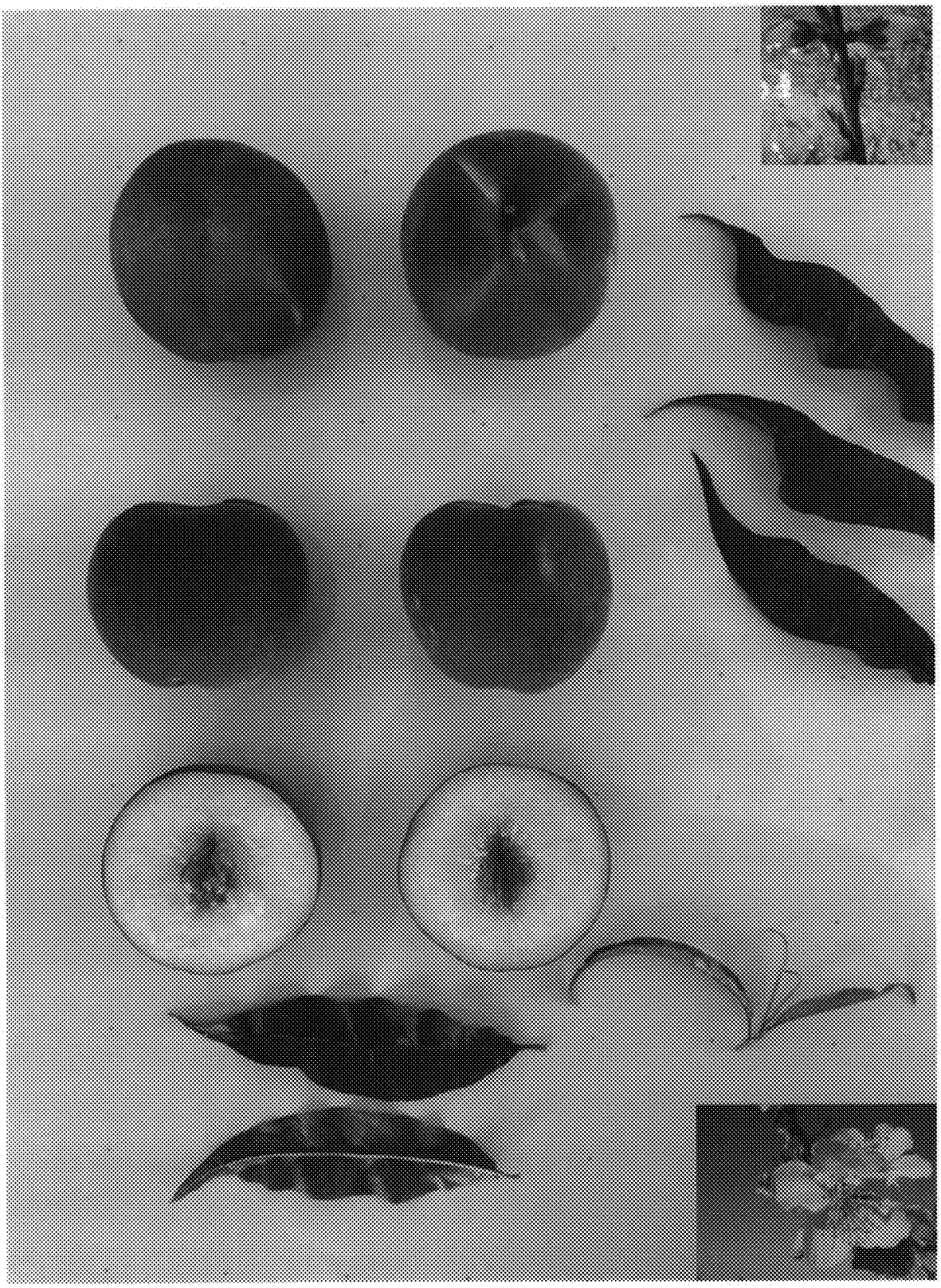

* * * * *